US009989451B2

(12) United States Patent
Cheong et al.

(10) Patent No.: US 9,989,451 B2
(45) Date of Patent: Jun. 5, 2018

(54) METHOD AND SYSTEM FOR MEASURING POROSITY OF PARTICLES

(71) Applicant: New York University, New York, NY (US)

(72) Inventors: Fook Chiong Cheong, New York, NY (US); Ke Xiao, Elmhurst, NY (US); David Pine, New York, NY (US); David G. Grier, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days. days.

(21) Appl. No.: 15/376,274

(22) Filed: Dec. 12, 2016

(65) Prior Publication Data

US 2017/0191920 A1    Jul. 6, 2017

Related U.S. Application Data

(62) Division of application No. 13/883,260, filed as application No. PCT/US2011/059400 on Nov. 4, 2011, now Pat. No. 9,519,129.

(60) Provisional application No. 61/410,739, filed on Nov. 5, 2010.

(51) Int. Cl.
| | |
|---|---|
| *G01N 15/08* | (2006.01) |
| *G02B 21/36* | (2006.01) |
| *G01N 21/45* | (2006.01) |
| *G01N 15/14* | (2006.01) |

(52) U.S. Cl.
CPC ....... *G01N 15/088* (2013.01); *G01N 15/1463* (2013.01); *G01N 21/453* (2013.01); *G02B 21/367* (2013.01); *G01N 2015/0846* (2013.01)

(58) Field of Classification Search
CPC .. G01N 15/08; G01N 15/1463; G01N 21/453; G01N 21/4133; G01N 21/47; G01N 2015/0846; G02B 1/367
USPC .......................................................... 348/79
See application file for complete search history.

(56) References Cited

U.S. PATENT DOCUMENTS

| | | | |
|---|---|---|---|
| 4,540,285 | A | 9/1985 | Amer |
| 5,146,086 | A * | 9/1992 | De .......................... G01N 15/08 250/253 |
| 5,373,727 | A | 12/1994 | Heller et al. |
| 2006/0029634 | A1 | 2/2006 | Berg et al. |

OTHER PUBLICATIONS

Lee et al. "Characterizing and tracking single colloidal particles with video holographic microscopy", Dec. 24, 2007 / vol. 15, No. 26 / Optics Express 18275.*

(Continued)

*Primary Examiner* — Thai Tran
*Assistant Examiner* — Nien-Ru Yang
(74) *Attorney, Agent, or Firm* — Foley & Lardner LLP

(57) ABSTRACT

A method for analyzing porosity of a particle and a medium disposed in the porosity of the particle. A video-holographic microscope is provided to analyze interference patterns produced by providing a laser source to output a collimated beam, scattering the collimated beam off a particle and interacting with an unscattered beam to generate the interference pattern for analyzation to determine the refractive index of the particle and a medium disposed in the porosity of the particle to measure porosity and the medium.

20 Claims, 6 Drawing Sheets

(56) References Cited

OTHER PUBLICATIONS

Cheong et al., "Holographic characterization of individual colloidal spheres' porosites." Soft Matter, Jun. 22, 2011, vol. 7, No. 15, pp. 6816-6819.
Lee et al., "Characterizing and tracking single colloidal particles with video holographic microscopy", Optics Express, Dec. 20, 2007, vol. 15, issue 26, pp. 18275-18282.
Lee et al., Characterizing and tracking single colloidal particles with video holographic microscopy, Optics Express, Dec. 20, 2007, vol. 15, No. 26, 8 pages.
PCT International Search Report, PCT Appln. No. PCT/US2011/059400, dated May 30, 2012, 4 pages.
Office Action for U.S. Appl. No. 13/883,260, dated Jan. 4, 2016, 12 pages.
Notice of Allowance for U.S. Appl. No. 13/883, 260, dated Aug. 5, 2016, 9 pages.

\* cited by examiner

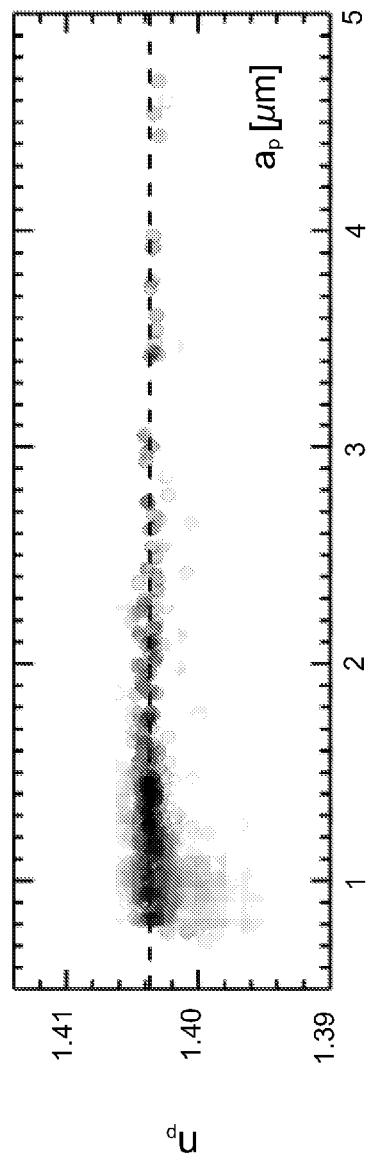
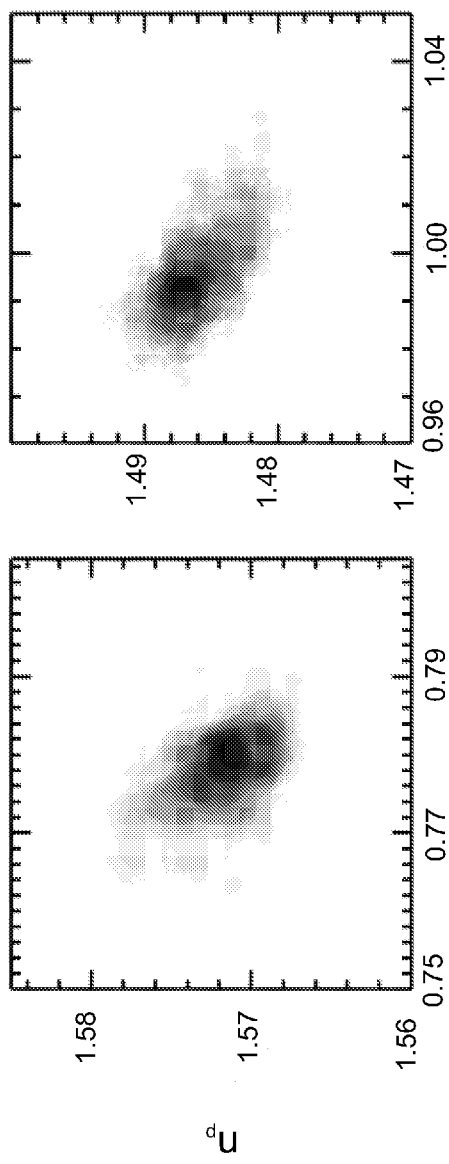
FIG. 4A
FIG. 4B
FIG. 4C

METHOD AND SYSTEM FOR MEASURING POROSITY OF PARTICLES

CROSS-REFERENCE TO RELATED PATENT APPLICATIONS

This application is a divisional of U.S. patent application Ser. No. 13/883,260, filed Nov. 4, 2011, which was the National Stage Entry of International Application No. PCT/US2011/59400, filed Nov. 4, 2011, which claims the benefit and priority to U.S. Application No. 61/410,739, filed Nov. 5, 2010, all of which are incorporated herein by reference in their entireties.

The U.S. Government has certain rights pursuant to grants from the National Science Foundation through Grant Number DMR-0820341 and in part by the NSF through Grant Number DMR-0922680.

The present invention is directed to an improved method and system for analyzing properties of particles including particle size, indices of refraction, controlling particle porosity development and particle porosity characterization measured by holographic characterization. More particularly the invention concerns a method, system and computerized method of analysis for characterization of particle porosity by determining refractive indices of particles, such as colloidal spheres, by holographic video microscopy.

BACKGROUND OF THE INVENTION

The properties of colloidal particles synthesized by emulsion polymerization typically are characterized by methods such as light scattering, whose results reflect averages over bulk samples. Therefore even as many applications advance toward single-sphere implementations, methods for characterizing colloidal spheres typically offer only sample-averaged overviews of such properties as spheres' sizes and porosities. Moreover, such characterization methods as mercury adsorption porosimetry, nitrogen isotherm porosimetry, transmission electron microscopy and X-ray tomography require preparation steps that may affect particles' properties. Consequently, such methods do not allow for determining porosity for individual particles, particularly in suspension nor allow characterization of porosity development in particles and can even modify particle properties. Consequently, a substantial need exists for a method and system for determining particle porosity and analyzing its development in particles.

SUMMARY OF THE INVENTION

The recent introduction of holographic characterization techniques now has enabled direct characterization of the radius and refractive index of individual colloidal spheres with very high resolution. Such article-resolved measurements, in turn, provide previously unavailable information on the distribution of properties in colloidal dispersions. We have used these techniques to be able to measure the porosity of individual colloidal spheres, and to probe the processes by which porosity develops during their synthesis.

The objects, aspects, variations and features of the invention will become more apparent and have a fuller understanding of the scope of the invention described in the description hereinafter when taken in conjunction with the accompanying drawings described hereinbelow.

BRIEF DESCRIPTION OF THE DRAWINGS

FIG. 4A illustrates a distribution of droplet sizes and refractive indexes for emulsified silicone oil in water; FIG. 4B shows anti-correlated properties of a monodisperse sample of emulsion polymerized silica spheres in water; and FIG. 4C shows equivalent results for a monodisperse sample of PMMA spheres in water (note for each of these figures the gray scale side bar indicator of FIG. 3C can be used to determine value levels);

DETAILED DESCRIPTION OF PREFERRED EMBODIMENTS

Figure 2A:
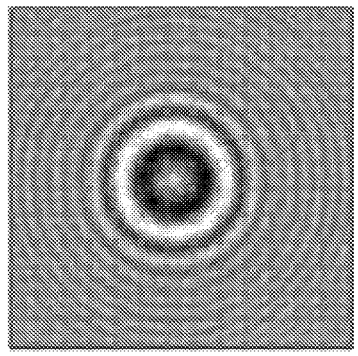
FIG. 2A illustrates a holographic video microscope image of a nominally 1.2 μm diameter polystyrene sphere in water.

The method and system includes an in-line holographic video microscope system 10 in which individual colloidal spheres are illuminated by the collimated beam 20 from a fiber-coupled diode laser 30 (iFlex Viper, λ=640 nm, 5 mW) on the stage of an otherwise conventional light microscope 40 (Nikon TE 2000U). Light 45 scattered by a sample particle 35, such as for example a sphere, interferes with the unscattered portion of the beam 20 in the focal plane of the microscope's objective lens 50 (Nikon Plan-Apo, 100×, numerical aperture 1.4, oil immersion). The preferred form of the system 10 includes eyepiece 70. The interference 55 pattern is magnified by the microscope system 10, and its intensity is recorded with a video camera 60 (NEC TI-324AII) at 30 frames/s and a resolution of 135 nm/pixel. The example in FIG. 2A shows the hologram of a polystyrene sphere dispersed in water.

Figure 1:
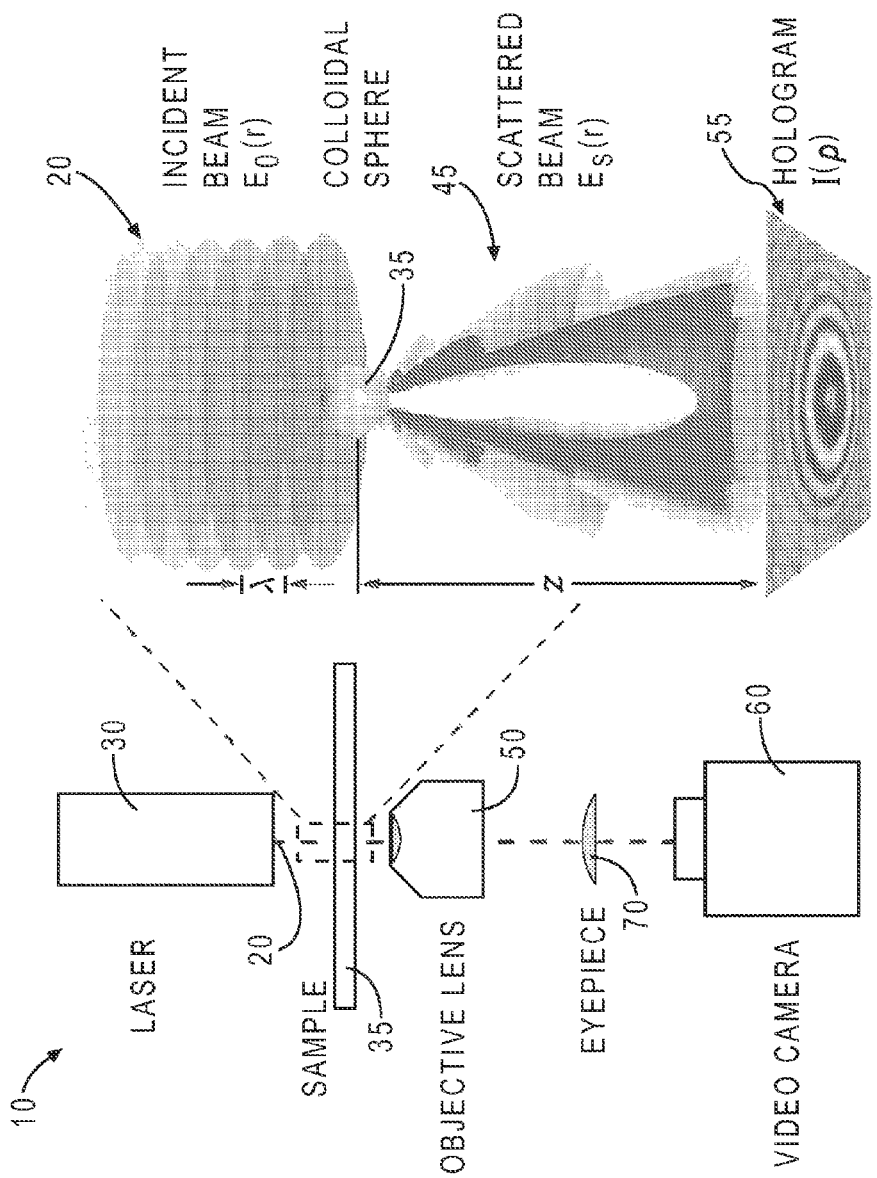
FIG. 1 shows an in-line holographic video microscope system.
Figure 2B:
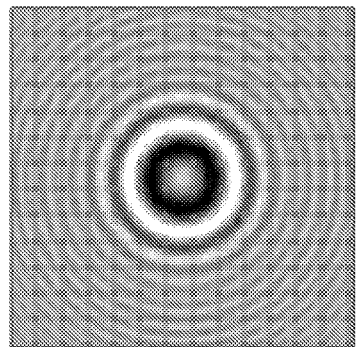
FIG. 2B shows a fit of the image in 2A to the predictions of Lorenz-Mie theory for the sphere's position, $\vec{r}_p(t)$, its radius, $a_p$, and its refractive index, $n_p$.

Each particle's image is digitized at a nominal 8 bits/pixel intensity resolution and analyzed using predictions of the Lorenz-Mie theory of light scattering to obtain the particle's position in three dimensions, its radius, and its complex refractive index. FIG. 2B shows the pixel-by-pixel fit to the measured hologram in FIG. 1. The microscope system 10 is defocused for these measurements so that each particle's interference pattern subtends a 100×100 pixel field of view. Motion blurring is minimized by setting the camera's exposure time to 0.1 ms and the illuminating laser's intensity is regulated to make optimal use of the recording system's dynamic range. Fitting to such a large amount of data reliably yields estimates for the adjustable parameters with part-per-thousand resolution.

Figure 2C:
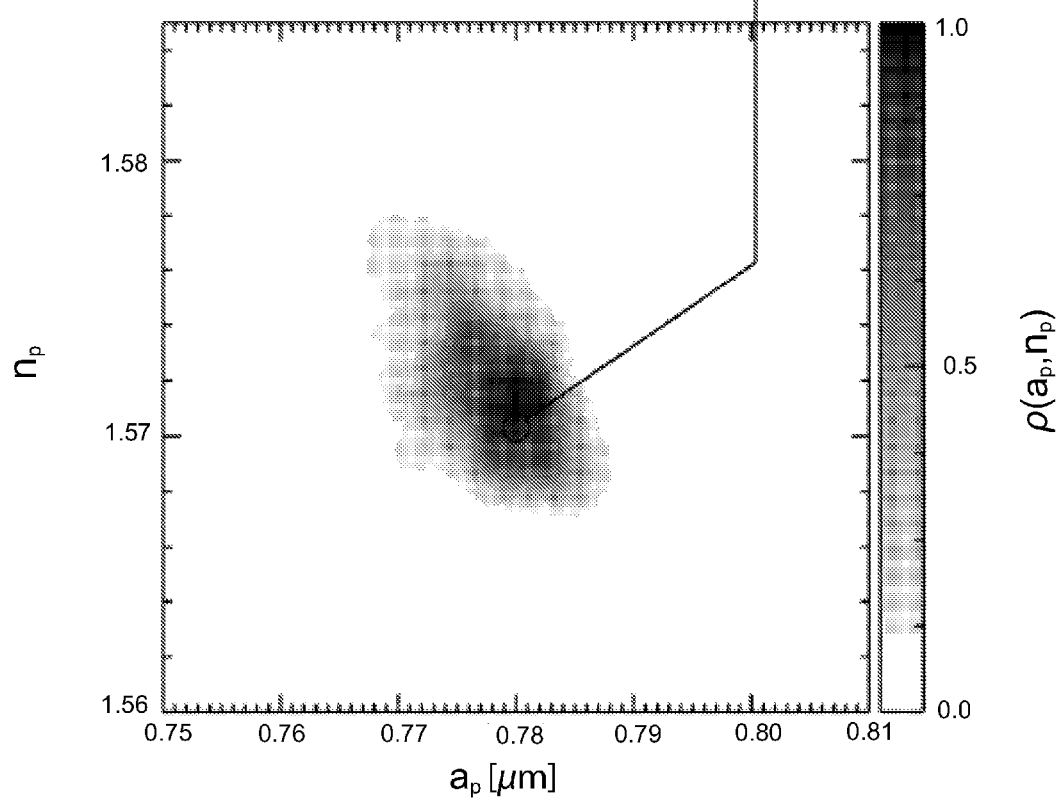
FIG. 2C shows a distribution of measured radii and refractive indexes for a randomly selected sample of 2,500 spheres such as the example in FIG. 2A; each point represents the result for one sphere and has distribution values of gray scale level as noted in the side bar of FIG. 2C, the relative probability density $\rho(a_p,n_p)$ for finding spheres of radius $a_p$ and refractive index $n_p$.

Hereinafter, we shall describe the method and system of the invention in the context of the particle being a sphere, although the method and system can be readily applied to any particle shape by well known modification of the Lorenz-Mie method or use of other well known analytical formalisms. The data in FIG. 2C were collected from 5,000 polystyrene spheres selected at random from a monodisperse sample (Duke Scientific, catalog number 5153, lot 26621). The suspension was diluted with deionized water so that no more than 10 spheres were in the field of view at any time, and was flowed in a microfluidic channel past the observation volume at a peak speed of 100 μm/s. The entire data set was acquired in 15 min. Each data point in FIG. 2C represents the radius and refractive index of a single sphere, with error bars comparable in size to the plot symbols. Individual symbols are shown for various gray scale levels according to the sample-estimated probability density $p(a_p, n_p)$ for finding a sphere with radius $a_p$ and refractive index $n_p$ (see side bar indicator of FIG. 3C for levels of values).

These results suggest a mean particle radius $a_p=0.778\pm0.007$ μm that is consistent with the manufacturer's specification. The mean refractive index $n_p=1.572\pm0.003$ is significantly smaller than the value of 1.5866 obtained for bulk polystyrene at the imaging wavelength. It is consistent with previous bulk measurements on colloidal polystyrene spheres.

More surprising is the distinct anti-correlation between radius and refractive index revealed by the data in FIG. 2C. Such a relationship could not have been detected with bulk probes, such as dynamic light scattering. It suggests that the larger particles in a sample are less optically dense than those on the smaller end of the distribution, and thus presumably more porous.

Figure 3A:
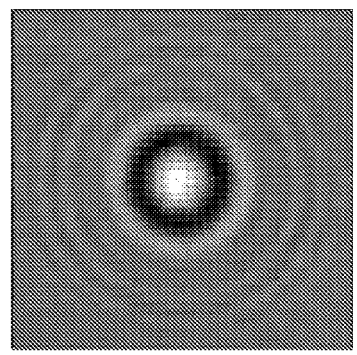
FIG. 3A shows a holographic video microscope image of a nominally 1.5 μm diameter silica sphere in water.
Figure 3B:
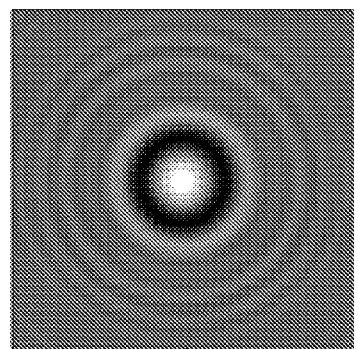
FIG. 3B shows a fit of the image in FIG. 3A to the predictions of Lorenz-Mie theory for the sphere's position, $\vec{r}_p(t)$, its radius, $a_p$, and its refractive index, $n_p$.
Figure 3C:
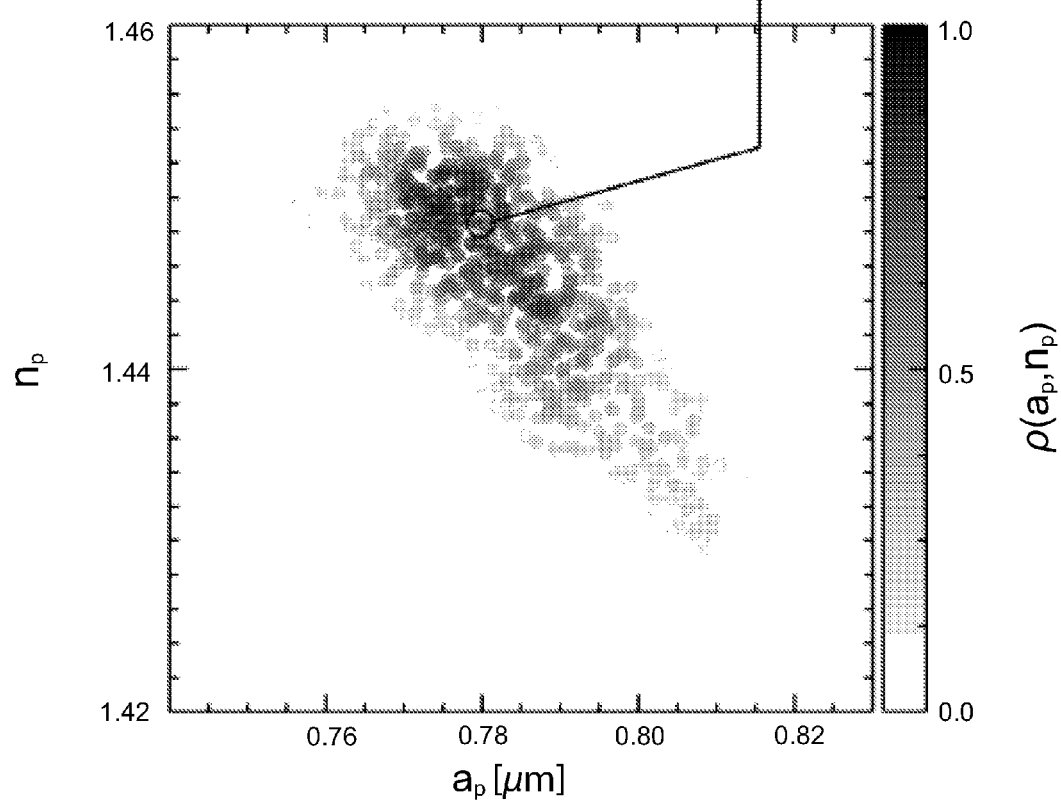
FIG. 3C shows distribution of measured radii and refractive indexes for a randomly-selected sample of 1,000 similar spheres, and each point represents the result for one sphere and value levels are determined by the gray scale side bar indicator of FIG. 3C for the relative probability density $\rho(a_p,n_p)$ for finding spheres of radius $a_p$ and refractive index $n_p$.

Each data point in FIG. 3C represents the radius and refractive index of a particular silica sphere, with error bars comparable in size to the plot symbol. The entire plot comprises results for 1,000 spheres selected at random from a monodisperse sample (Duke Scientific, catalog number 8150), with plot symbols in gray scale (see side bar for indicator of levels of values) according to the sample-estimated relative probability density; $\rho(a_p,n_p)$, for finding a sphere of radius $a_p$ and refractive index $n_p$. These data were obtained by flowing the aqueous dispersion through a microfluidic channel past the observation volume at a peak speed of 100 μm/2. This is slow enough that motion blurring has no measurable influence on the characterization results. The suspension was diluted with deionized water to the point that no more than 10 spheres were in the field of view at any time, thereby minimizing overlap between neighboring spheres' scattering patterns. The entire data set was acquired in 5 min.

The spheres' average radius $a_p=0.786\pm0.015$ μm is consistent with the manufacturer's specification. By contrast, the mean refractive index $n_p=1.444\pm0.007$ is significantly smaller than the value of 1.4568 for fused silica at the imaging wavelength. Similar discrepancies have been reported in previous measurements on dispersions of colloidal silica spheres.

The data in FIG. 3C also reveal a distinct anticorrelation between radius and refractive index. Such a relationship could not have been detected with bulk probes, such as dynamic light scattering. It suggests that the larger particles in a sample are less optically dense than those on the smaller end of the size distribution.

The data in FIG. 4A-4C demonstrate that observed anticorrelation is not an artifact of the technique, but rather is a common feature of colloidal samples synthesized by emulsion polymerization. FIG. 4A shows results for a very polydisperse sample of silicone oil droplets (Dow Corning 200 fluid) stabilized with Pluronic L92 surfactant in water. Although the range of particle radii is large, the distribution of refractive indexes are consistent with a bulk value of $n_p=1.404\pm0.002$ within the part-per-thousand resolution estimated from the uncertainty in the fitting parameters. This is reasonable because the droplets all are composed of the identical material and are not at all porous and contain fluid at bulk density. Results for smaller droplets are more strongly influenced by the surfactant, which has a bulk refractive index of 1.38. Variation in surfactant coverage thus causes variation in the apparent refractive index. The peak of the probability distribution nevertheless falls within error estimates of the refractive index of bulk silicone oil for all sizes. The lack of covariance between measured radii and refractive indexes in this sample therefore demonstrates the absence of instrumental or analytical bias in the methods used to study emulsion polymerized colloidal samples.

The data in FIGS. 4B and 4C show additional results for monodisperse aqueous dispersions of colloidal silica spheres (Duke Scientific, catalog number 8150) and colloidal polymethymethacrylate (PMMA, Bangs Laboratory, catalog number PP04N) spheres, respectively, both synthesized by emulsion polymerization. These samples both display anti-correlations between size and refractive index comparable to that of the polystyrene sample in FIGS. 2A-2C, but with different correlation coefficients. Observations on similar samples obtained from different manufacturers reveal a range of apparent correlation coefficients that may reflect differing growth conditions.

In view of the above generalization, chemically synthesized colloidal spheres are known to be less dense than the bulk material from which they are formed. The difference may take the form of voids that can be filled with other media, such as the fluid in which the spheres are dispersed. A sphere's porosity p is the fraction of its volume comprised of such pores. If the pores are distributed uniformly throughout the sphere on lengthscales smaller than the wavelength of light, their influence on the sphere's refractive index may be estimated with effective medium theory. Specifically, if the bulk material has refractive index $n_1$ and the pores have refractive index $n_2$, then the sphere's porosity is related to its effective refractive index $n_p$ by the Lorentz-Lorenz relation.

$$p = \frac{f(n_p) - f(n_2)}{f(n_1) - f(n_2)}, \tag{1}$$

where $f(n)=(n^2-1)(n^2+2)$. Provided that $n_2$ can be determined, Eqn. (1) provides a basis for measuring the porosity of individual colloidal spheres in situ.

The value of $n_2$ is readily obtained in two limiting cases. If the suspending medium wets the particle, then it also is likely to fill its pores. In that case, we expect $n_2=n_m$, where $n_m$ is refractive index of the medium. If, at the other extreme, the particle repels the solvent, then the pores might better be treated as voids with $n_2=1$.

We can model the growth of a colloidal sphere as the accretion of N monomers of specific volume v. Assuming a typical sphere to be comprised of a large number of monomers, and further assuming that all of the spheres in a dispersion grow under similar conditions, the probability distribution for the number of monomers in a sphere is given by the central limit theorem:

$$P_N(N) = \frac{1}{\sigma_N}\sqrt{\frac{2}{\pi}}\exp\left(-\frac{[N-N_0]^2}{2\sigma_N^2}\right), \quad (2)$$

where $N_0$ is the mean number of monomers in a sphere and $\sigma_N^2$ is the variance in that number.

Were each sphere to grow with optimal density, its volume would be Nv. Development of porosity p during the growth process increases the growing sphere's volume to $$V_p = \frac{4}{3}\pi\ a_p^3 = \frac{vN}{1-p}, \quad (3)$$

The probability distribution for finding a sphere of volume V therefore depends on the porosity:

$$P(V_p | p) = \frac{1-p}{\sigma_V}\sqrt{\frac{2}{\pi}}\exp\left(-\frac{[V_p(1-p)-N_0v]^2}{2\sigma_V^2}\right), \quad (4)$$

where $\sigma_V=v\sigma_N$. An individual sphere's porosity, in turn, can be estimated from its measured refractive index through the Lorentz-Lorenz relation (Eqn. (1) above) where $n_1$ is the refractive index of the sphere at optimal density, $n_2$ is the refractive index of the surrounding fluid medium, and $f(n)=(n^2-1)/(n^2+2)$. If the porosity develops uniformly as a particle grows, then the probability distribution $P_p(p)$ of particle porosities will be independent of size. In that case, the joint probability $$P(V_p,p)=P_v(V_p|p)P_p(p) \quad (5)$$

may be factored into a term that depends only on porosity p and another that depends only on the rescaled volume $V_p(1-p)$. In another form of the invention other analytical methods can be used to measure porosity, such as the "parallel model" where $n_p=p_n(1-p)n_2$ or the series model where $1/n_p=p/n_1+(1-p)n_2$.

If, furthermore, a sphere's porosity develops uniformly as it grows, Eqs. (3) and (4) suggest that the rescaled volume, $V_p(1-p)$, should be independent of porosity p. This is indeed the case for the data in FIG. 2C whose marked anti-correlation largely (although not completely) disappears when replotted in FIG. 5A. Here, we have used $n_1=1.5866$ for bulk polystyrene and $n_2=1.3324$ for water. Comparably good results are obtained with the silica spheres from FIG. 4B ($n_1=1.4568$) and the EMMA spheres from FIG. 5C ($n_1=1.4887$).

Figures 5A, 5B, 5C:
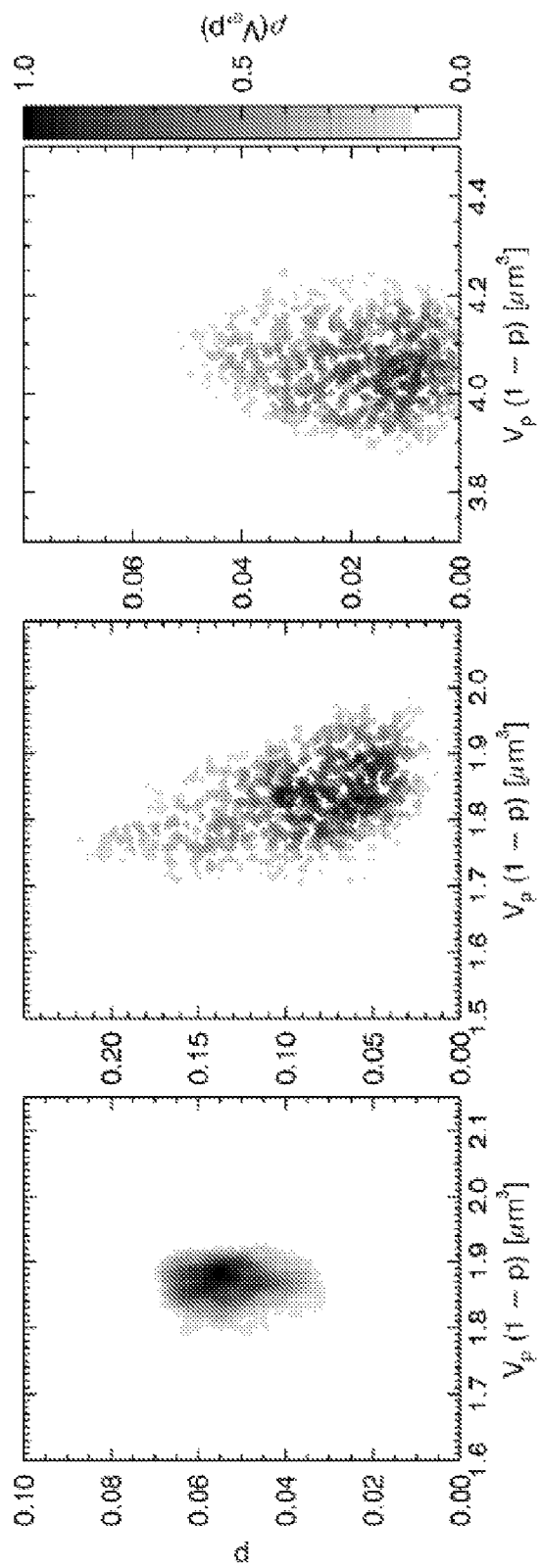
FIG. 5A illustrates distribution of the scaled volumes and porosities of individual colloidal spheres composed of polystyrene (from the data in FIG. 2C)
FIG. 5B shows silica (see FIG. 4B)
FIG. 5C shows PMMA (see FIG. 4C) (note for each of these figures the gray scale side bar indicator of FIG. 3C can be used to determine value levels)

Small residual anti-correlations between scaled volume and porosity, particularly evident in the silica data in FIG. 5B, primarily arise in the tails of the size and porosity distribution. Considering only those spheres in the upper half of the relative probability distributions in FIGS. 5A-5C remove any statistically significant relationship as measured by Kendall's rank correlation test. The residual covariance between p and $V_p(1-p)$ is less than 10-4 for the high-probability fraction in all three samples. The observed correlations in the complete data sets therefore arise primarily in the tails of the distribution, and may reflect real temporal or spatial variations in the growth conditions. The absence of correlations in the highest-probability sample is consistent with the simplified model for the development of porosity, and also with the use of effective medium theory for interpreting individual spheres' light-scattering properties. More specifically, our neglect of radial gradients in porosity appears to be justified for the samples we have investigated.

Figures 6A, 6B, 6C:
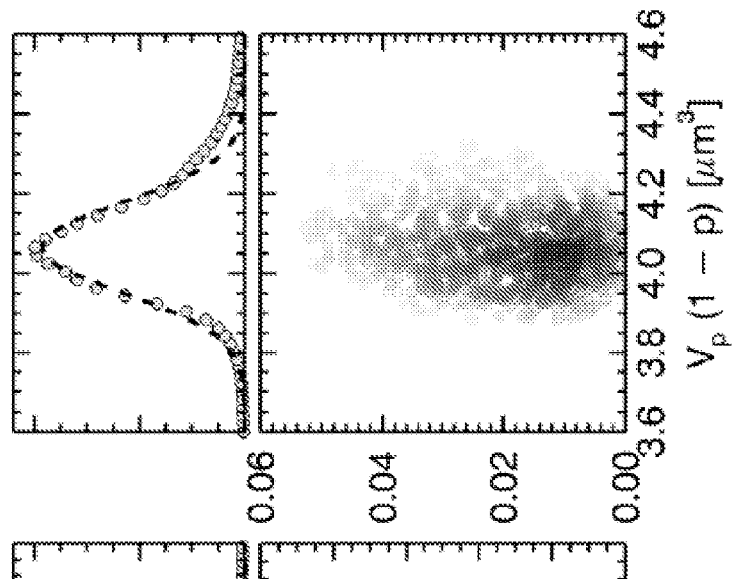
FIG. 6A shows distribution of the scaled volumes and porosities of individual colloidal spheres composed of (a) silica (from the data in FIG. 3C.
FIG. 6B shows styrene (FIGS. 3B and 3C) and PMMA (FIG. 6C), all dispersed in water; lower distributions were computed for the value of $n_2$ that eliminates correlations between $\rho$ and $V_p(1-p)$; upper plots show the distribution of scaled particle volumes for these optimal values, together with fits to Gaussian distributions (note for each of these figures the gray scale side bar indicator of FIG. 3C can be used to determine value levels).

Within the assumptions of the model of Eqns. (1)-(5), the correct choice for $n_2$ should decorrelate the rescaled volume $V_p(1-p)$ and the porosity p. We therefore select the value of $n_2$ for which the Pearson's correlation coefficient between p and $V_p(1-p)$ vanishes. The scatter plots in FIGS. 6A-6C show the distribution of particle volumes and porosities obtained with these optimal values of $n_2$. The upper plots show estimates for $P_v(V_p\backslash p)$ obtained by integration over ρ, together with fits to the anticipated Gaussian form. Agreement is good enough in all three cases to justify the use of eqn (4) to interpret the experimental data.

The results for the silica sample in FIG. 6A were obtained using $n_1=1.4568$ for fused silica. The estimated value of $n_2=1.31\pm0.03$ is consistent with the value of 1.3324 for water at the imaging wavelength. This suggests that pores in the hydrophilic silica spheres are filled with water. The associated mean porosity, $p=0.092\pm0.004$, is comparable to the 8 percent porosity determined by low-temperature nitrogen adsorption for similar samples.

The equivalent results for the polystyrene sample in FIG. 6B were obtained using $n_1=1.5866$ for bulk polystyrene. In this case, the estimate value of $n_2=1.13\pm0.05$ is substantially smaller than the refractive index of either water or styrene. Rather than solvent-filled voids, the pores in the spheres seem rather to represent density fluctuations in the cross-linked polymer matrix. The failure of water to invade these pores is consistent with the hydrophobicity of polystyrene. With these choices for $n_1$ and $n_2$, the sample-averaged porosity is estimated to be $p=0.054\pm0.008$.

More surprisingly, the results for water-borne PMMA spheres plotted in FIG. 6C yield $n_2=1.33\pm0.01$, and therefore suggest that the spheres' pores are filled with water, even though PMMA is hydrophobic. The porosity, $p=0.02\pm0.01$, estimated using $n_1=1.4887$ for bulk PMMA, is comparable to previously reported values for similar spheres. Whereas, the polystyrene spheres appear to exclude water, the substantially less porous PMMA spheres seem to imbibe it. These observations suggest either that the two samples have substantially different pore morphologies, or else that hydrophilic groups are present within the pores of the PMMA sample.

The values obtained for single-particle porosities should be interpreted carefully and in some cases account for inhomogeneity in a particle's porosity. In some embodiments, the pores are assumed to be substantially filled with the same fluid in which the spheres are dispersed, and furthermore that the imbibed fluid retains its bulk refractive index. Departures from these assumptions can possibly give rise to some errors in the estimated porosity values. Even though single-particle values for $n_p$ are believed to be both precise and accurate, the precision of the porosity distributions in the previous embodiment needs to be carefully constructed and evaluated.

Correlations in the radii and refractive indexes of colloidal spheres measured through holographic particle characterization can be ascribed to porosity. Holographic characterization, therefore, can be used to assess the porosity of individual colloidal spheres and to gain insight into the medium filling their pores.

The present implementation uses sample averages to infer the refractive index of the medium filling the individual spheres' pores. Given this parameter, the porosity can be estimated for each sphere individually. The need to aggregate data from multiple particles could be eliminated by performing holographic characterization measurements in multiple wavelengths simultaneously. The resulting spectroscopic information, in principle, could be used to characterize both the porosity of a single sphere and also the medium filling its pores in a single snapshot.

Particle-resolved porosimetry probes the mechanisms by which porosity develops in samples of emulsion-polymerized colloidal spheres. For the samples we have studied, porosity appears to have developed uniformly as the particles grew, both within individual spheres, and throughout the sample as a whole. Differences between results for polystyrene and PMMA samples point to possible differences in the shapes or properties of their pores.

Holographic particle characterization can therefore be used to assess the porosity of individual colloidal particles and insights into the methods by which porosity develops in samples of emulsion-polymerized colloidal spheres and other particle shapes. For the variety of samples we have studied, porosity appears to develop with a probability distribution that is largely independent of the distribution of monomer number in the spheres. This leads to an apparent anti-correlation in the distribution of particles' radii and refractive indexes, which is stronger in more porous materials and is entirely absent in fully dense spheres. These observations, in turn, have ramifications for possible uses of emulsion polymerized colloidal particles in such applications as colloidal photonics.

In another aspect of the invention a conventional computer system can execute computer software stored in an appropriate memory, such as a ROM or RAM memory, embodying the analytical methodologies set forth hereinbefore to determine porosity of the subject particles.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of analyzing characteristics of a particle in suspension, comprising the steps of:
    providing a particle in a suspension medium;
    providing a video holographic microscope;
    providing a laser source for producing a collimated output beam;
    scattering the collimated output beam off the particle to generate a scattered beam and a combination of the scattered beam and an unscattered portion of the output beam to generate an interference pattern;
    recording intensity of the interference pattern for analysis;
    analyzing the interference pattern to determine refractive index of the particle; and
    comparing characteristics of an average of a bulk form of the material composing the particle to the particle refractive index to characterize parameters of the particle and the suspension medium.

2. The method as defined in claim 1 wherein the step of analyzing comprises determining the refractive index and then performing the comparing step to establish at least one of porosity of the particle and character of the suspension medium disposed in pores of the particle.

3. The method as defined in claim 1 wherein the step of analyzing the interference pattern comprises applying a Lorenz-Mie formalism to determine the refractive index of the particle.

4. The method as defined in claim 1 further including the step of analyzing the interference pattern during growth of the particle, thereby enabling characterization of development of porosity in the particle.

5. The method as defined in claim 3 wherein the Lorenz-Mie formalism comprises, $$I(r)=|E_0(r)+E_0(r_p)f_s(k(r-r_p))|^2,$$

where I(r) is intensity of the interference pattern recorded at position r, $E_0(r)$ is the electric field of the output laser at position r, $r_p$ is the position of the particle, k is the wavenumber of the light, and $f_s(kr)$ is the Lorenz-Mie scattering function that describes scattering of light by the particle and wherein the Lorenz-Mie scattering function depends on radius of the particle effective refractive index of the particle.

6. The method as defined in claim 5 where the effective refractive index $n_p$ of the particle depends on refractive index of the bulk form of the material from which the particle is composed, porosity of the particle, and refractive index of the medium that fills the pores within the particle.

7. The method as defined in claim 6 where the porosity p of the particle is related to the effective refractive index of the particle, $n_p$, the refractive index $n_1$ of the bulk form of the material from which the particle is composed and the refractive index $n_2$ of the material filling the particle's pores according to $$p = \frac{f(n_p) - f(n_2)}{f(n_1) - f(n_2)},$$

where $$f(n) = \frac{n^2 - 1}{n^2 + 2}.$$

8. The method as defined in claim 1 further including a computer system for executing computer software to carry out the steps of analyzing the interference pattern and comparing the refractive index of the bulk form of the material to the refractive index of the particle.

9. A method of analyzing a medium disposed in a particle in suspension, comprising the steps of:
providing a video holographic microscope;
providing a laser source for producing a collimated output beam;
scattering the collimated output beam off the particle to generate a scattered beam and a combination of the scattered beam and an unscattered portion of the output beam to generate an interference pattern;
recording intensity of the interference pattern for analysis;
analyzing the interference pattern to determine refractive index of the particle; and
comparing refractive index of an average of a bulk form of the material of the particle to the refractive index of the particle in the suspension to determine a measure of the medium disposed in porosity of the particle.

10. The method as defined in claim 9 wherein the step of analyzing the interference pattern comprises applying a Lorenz-Mie formalism to determine the refractive index of the particle containing the medium.

11. The method as defined in claim 9 further including the step of analyzing the interference pattern during growth of the particle, thereby enabling characterization of development of the medium disposed in the porosity in the particle.

12. The method as defined in claim 10 wherein the Lorenz-Mie formalism comprises, $$I(r)=|E_0(r)+E_0(r_p)f_s(k(r-r_p))|^2;$$

where I(r) is intensity of the interference pattern recorded at position r, $E_0(r)$ is the electric field of the output laser at position r, $r_p$ is the position of the particle is the refractive index of the medium disposed in the porosity of the particle, k is the wavenumber of the light, and $f_s(kr)$ is the Lorenz-Mie scattering function that describes scattering of light by the particle, wherein the Lorenz-Mie scattering function depends on radius of the particle effective refractive index of the particle.

13. The method as defined in claim 9 further including a computer system for executing computer software to carry out the steps of analyzing the interference pattern and comparing the refractive index of the bulk form of the material to the refractive index of the particle with the medium disposed in the porosity.

14. The method as defined in claim 12 wherein a refractive index of the medium disposed in the porosity of the particle is selected from the group consisting of the refractive index of a suspension fluid wetting the particle and a refractive index of the medium disposed in the porosity of the particle is equal to wherein the porosity of the particle is a void.

15. A method of analyzing a particle in suspension, comprising the steps of:
providing a video holographic microscope;
providing a laser source for producing a collimated output beam comprised of a plurality of different wavelengths of light;
scattering the collimated output beam off the particle by simultaneously using the plurality of different wavelengths of light to generate a plurality of scattered beams and a combination of the scattered beams and an unscattered portion of the output beam to generate a plurality of interference patterns;
recording intensity of the interference pattern;
analyzing the interference patterns to determine refractive index of the particle; and
determining a measure of at least one of porosity of the particle and a medium disposed in the porosity of the particle.

16. The method as defined in claim 15 wherein the step of analyzing the interference pattern comprises applying a Lorenz-Mie formalism to determine at least one of the refractive index of the particle and the medium disposed in the porosity of the particle.

17. The method as defined in claim 15 further including the step of analyzing the interference pattern during growth of the particle, thereby enabling characterization of development of the porosity in the particle and the medium disposed in the porosity of the particle.

18. The method as defined in claim 16 wherein the Lorenz-Mie formalism comprises, $$I(r)=|E_0(r)+E_0(r_p)f_s(k(r-r_p))|^2;$$

where I(r) is intensity of the interference pattern recorded at position r, $E_0(r)$ is the electric field of the output laser at position r, $r_p$ is the position of the particle, k is the wavenumber of the light, and $f_s(kr)$ is the Lorenz-Mie scattering function that describes scattering of light by the particle, wherein the Lorenz-Mie scattering function depends on radius of the particle and on effective refractive index of the particle.

19. The method as defined in claim 15 further including a computer system for executing computer software to carry out the steps of analyzing the interference pattern and comparing the refractive index of a bulk form of a material of the particle to the refractive index of the particle.

20. The method as defined in claim 18 wherein the medium disposed in the porosity of the particles is selected from the group consisting of refractive index of the suspension fluid wetting the particle, and wherein the porosity of the particle is a void.

* * * * *